（12) United States Patent
Nadolski et al.

(10) Patent No.: US 10,543,304 B2
(45) Date of Patent: Jan. 28, 2020

(54) BLOOD TREATMENT APPARATUS WITH MULTIPLE AXIS MONITOR MOUNT

(71) Applicant: GAMBRO LUNDIA AB, Lund (SE)

(72) Inventors: Timothy Nadolski, Maple Grove, MN (US); John O'Mahony, Maple Grove, MN (US); Stephen R. Fyten, Ramsey, MN (US); Michael L. Casmey, Plymouth, MN (US); Steve Bernard, Eden Prairie, MN (US)

(73) Assignee: Gambro Lundia AB, Lund (SE)

( * ) Notice: Subject to any disclaimer, the term of this patent is extended or adjusted under 35 U.S.C. 154(b) by 75 days.

(21) Appl. No.: 15/775,046

(22) PCT Filed: Nov. 16, 2016

(86) PCT No.: PCT/US2016/062219
§ 371 (c)(1),
(2) Date: May 10, 2018

(87) PCT Pub. No.: WO2017/087481
PCT Pub. Date: May 26, 2017

(65) Prior Publication Data
US 2018/0318487 A1    Nov. 8, 2018

Related U.S. Application Data

(60) Provisional application No. 62/256,876, filed on Nov. 18, 2015.

(51) Int. Cl.
*A61M 1/16*        (2006.01)
*G16H 40/63*      (2018.01)

(52) U.S. Cl.
CPC ........ *A61M 1/1601* (2014.02); *A61M 1/1621* (2014.02); *G16H 40/63* (2018.01); *A61M 2205/505* (2013.01); *A61M 2209/08* (2013.01)

(58) Field of Classification Search
CPC .............. A61M 1/1601; A61M 1/1621; A61M 2205/502; A61M 2205/505; A61M 2209/08; G16H 40/63
See application file for complete search history.

(56) References Cited

U.S. PATENT DOCUMENTS 5,788,851 A    8/1998   Kenley
6,143,181 A    11/2000  Falkvall
(Continued)

FOREIGN PATENT DOCUMENTS

CN    0204521757    8/2015
EP    0755273 B1    10/1999
(Continued)

OTHER PUBLICATIONS

PCT/US2016/062219 International Preliminary Report on Patentability dated May 31, 2018 (10 pages).
(Continued)

*Primary Examiner* — Dirk R Bass
(74) *Attorney, Agent, or Firm* — Mueting, Raasch & Gebhardt, P.A.

(57) ABSTRACT

Extracorporeal blood treatment apparatus (10) having a monitor (20) mounted on a multiple axis monitor mount (30) are described herein along with methods of rotating the monitor about multiple axes (31, 33). In one or more embodiments, the monitor mount is water resistant to facilitate cleaning of the blood treatment apparatus.

22 Claims, 11 Drawing Sheets

(56) References Cited

U.S. PATENT DOCUMENTS

| | | |
|---|---|---|
| 6,146,526 A | 11/2000 | Pandolfo |
| 7,074,182 B2 | 7/2006 | Bertolero |
| 9,319,110 B2 | 4/2016 | Kopychev |
| 2009/0284108 A1 | 11/2009 | Catellano |
| 2010/0271296 A1 | 10/2010 | Kopychev |
| 2018/0015215 A1 | 1/2018 | Peters |

FOREIGN PATENT DOCUMENTS

| | | |
|---|---|---|
| EP | 0959913 B1 | 10/2003 |
| EP | 0959980 B2 | 2/2012 |
| EP | 2046416 B1 | 9/2015 |
| WO | WO 2017/087481 A1 | 5/2017 |

OTHER PUBLICATIONS

PCT/US2016/062219 International Search Report and Written Opinion dated Jan. 31, 2017 (15 pages).

BLOOD TREATMENT APPARATUS WITH MULTIPLE AXIS MONITOR MOUNT

CROSS-REFERENCE TO RELATED APPLICATION

This application is a U.S. National Stage Application of International Application No. PCT/US2016/062219, filed Nov. 16, 2016 and published in English on May 26, 2017 as International Publication No. WO 2017/087481 A1, which claims the benefit under 35 U.S.C. 119(e) of U.S. Provisional Application Ser. No. 62/256,876, filed on 18 Nov. 2015, which are all incorporated herein by reference in their entirety.

Extracorporeal blood treatment apparatus having a multiple axis monitor mount for mounting a display used during operation of the extracorporeal blood treatment apparatus are described herein along with methods of rotating the monitor.

Extracorporeal blood treatment apparatus remove blood from a patient, treat the blood outside the patient (to extract undesirable matter or molecules from and/or add beneficial matter or molecules to the blood), and return the treated blood to the patient after treatment. The extracorporeal blood treatment apparatus often includes multiple pumps, valves, switches, sensors, etc. that must be controlled by a control unit and software.

The operator of the extracorporeal blood treatment apparatus must be provided with a way to interface with the control unit. In one or more embodiments, commands are entered via a monitor equipped with a touchscreen that displays a GUI (Graphical User Interface) they can be used to enter commands into the control unit to control the extracorporeal blood treatment apparatus. Although such interfaces may be useful, they may, in one or more embodiments, result in a larger housing for the extracorporeal blood treatment apparatus which may pose challenges for transportation and storage of the units.

SUMMARY

Extracorporeal blood treatment apparatus having a monitor mounted on a multiple axis monitor mount are described herein along with methods of rotating the monitors about multiple axes. In one or more embodiments, the monitor mount is water resistant to facilitate cleaning of the blood treatment apparatus.

The extracorporeal blood treatment apparatus described herein include monitors affixed to the top surface of the housings of the extracorporeal blood treatment apparatus by monitor mounts. In one or more embodiments, using a monitor mount to attach a monitor to the top surface of the housing places the monitor (and, therefore, any GUI displayed on a display surface of the monitor) at a height that is convenient for an operator to view the GUI and, if the monitor is a touchscreen monitor, to input commands by touching various control points on the display surface of the monitor.

In one or more embodiments, it may be necessary for the operator to perform tasks on different sides of the machine (e.g., front, left and/or right sides) and, while performing those tasks, the operator may need to view the display screen and, if the display screen is a touchscreen, potentially input one or more commands for the control unit controlling the extracorporeal blood treatment apparatus. Rotation of the monitor about a swivel axis that is oriented vertically may, therefore, offer potential advantages to an operator while working on different sides of the extracorporeal blood treatment apparatus described herein because the monitor may be rotated such that the display surface faces the operator regardless of which side of the apparatus they are working on.

In addition to allowing rotation about a vertically oriented swivel axis, the monitor mounts used in connection with the extracorporeal blood treatment apparatus described herein may also allow for rotation of the monitor about a tilt axis that is oriented transverse to the swivel axis. Rotation of the monitor about a tilt axis may allow an operator to adjust the orientation of the display surface so that it is more easily viewed by, e.g., operators of different heights.

In one or more embodiments, transporting the extracorporeal blood treatment apparatus described herein in a healthcare facility may pose challenges if the height of the machine interferes with the vision of a person transporting the machine. In one or more embodiments of the extracorporeal blood treatment apparatus described herein, the monitor mount may be configured to allow rotation of the monitor about the tilt axis such that the display surface can be rotated from a generally vertical orientation to a stowed position in which the display surface of the monitor is oriented generally horizontal. In one or more embodiments, the display surface of the monitor may face the top surface of the housing or may face away from the top surface of the housing of the extracorporeal blood treatment apparatus when in a generally horizontal orientation. In that stowed configuration, the monitor typically provides a much lower profile and, therefore, may offer a significantly improved view to an operator moving the extracorporeal blood treatment apparatus through a healthcare facility.

Routing of cabling from the monitor to the control unit located within the housing may be problematic if the cabling is routed such that it is subject to repeated flexing, tension, and/or compression that may cause damage that results in short or open circuits. In one or more embodiments of the extracorporeal blood treatment apparatus described herein, stress on the cabling extending between the monitor and a control unit in the housing of the extracorporeal blood treatment apparatus may be reduced by routing the cabling such that a segment of the cabling is generally aligned along the tilt axis before turning to enter the housing of the extracorporeal blood apparatus, where it is generally aligned along the swivel axis. Such routing of the cabling may reduce torsional forces applied to the cabling during rotation of the monitor about both the swivel and tilt axes.

In those embodiments in which the monitor mounted on the extracorporeal blood treatment apparatus is a touchscreen, control over the force required to rotate the monitor about the swivel and tilt axes may be helpful to prevent movement of the monitor when an operator is entering commands on a GUI displayed on the touchscreen. In one or more embodiments, the monitor mount may be configured to provide selected levels of friction to control rotation of the monitor.

The extracorporeal blood treatment apparatus described herein may require cleaning and disinfecting of all surfaces of the apparatus using various liquid cleaning solutions. In general, those cleaning solutions should be prevented from entering the housing of the extracorporeal blood treatment apparatus. As a result, the monitor mount used to secure a monitor on the extracorporeal blood treatment apparatus housing may, in one or more embodiments, be water resistant to limit the entry of liquids into the housing.

In one aspect, an extracorporeal blood treatment apparatus as described herein may include: one or more pumps located on a front face of a housing, wherein the one or more pumps are configured to move blood and a treatment solution during extracorporeal blood treatment; a monitor comprising a display surface configured to display visual images thereon; and a monitor mount comprising a base attached to a top surface of the housing and a monitor arm attached to base and the monitor. The monitor is positioned above the base and the top surface of the housing, and wherein the monitor arm is configured to: rotate about a swivel axis that is oriented vertically through the base and the top surface of the housing such that the monitor can be rotated between a front-facing position in which the display surface faces the same direction as the front face of the housing and one of a left-facing position in which the display surface faces the same direction as a left side of the housing and a right-facing position in which the display surface faces the same direction as a right side of the housing; rotate about a tilt axis oriented transverse to the swivel axis, wherein the tilt axis is located above the base and the top surface of the housing, wherein the monitor is configured to rotate about the tilt axis between a stowed position and an operating position, wherein in the stowed position the display surface of the monitor is oriented in a plane that is generally transverse to the swivel axis, wherein in the operating position the display surface of the monitor is oriented in a plane that is generally aligned with the swivel axis. The extracorporeal blood treatment apparatus also includes a control unit located within the housing and operably connected to the one or more pumps, wherein the control unit is configured to operate the one or more pumps to move blood and a treatment solution and the monitor; and a first cable connecting the monitor to the control unit, wherein the first cable comprises a first segment generally aligned with the tilt axis and a second segment generally aligned with the swivel axis, wherein the first segment is closer to the monitor that the second segment, and wherein the second segment is closer to the control unit than the first segment, and further wherein the second segment of the first cable passes into the housing.

In one or more embodiments of the extracorporeal blood treatment apparatus described herein, the apparatus comprises a second cable connecting the monitor to the control unit, wherein the first cable and the second cable comprise a cable bundle that bifurcates into the first cable and the second cable between the monitor and the control unit, wherein the second cable comprises a first segment generally aligned with the tilt axis and a second segment generally aligned with the swivel axis, wherein the first segment of the second cable is closer to the monitor that the second segment, and wherein the second segment of the second cable is closer to the control unit than the first segment of the second cable, and further wherein the second segment of the second cable passes into the housing, and further wherein the first segments of the first cable and the second cable are located on opposite sides of the swivel axis. In one or more embodiments, the first cable and the second cable combine to reform the cable bundle in the housing. In one or more embodiments, the first segment of the first cable is symmetrical about the swivel axis with the first segment of the second cable, and wherein the second segment of the first cable is symmetrical about the swivel axis with the second segment of the second cable.

In one or more embodiments of the extracorporeal blood treatment apparatus described herein, the monitor arm is configured to rotate about the swivel axis between both the left-facing position and the right-facing position.

In one or more embodiments of the extracorporeal blood treatment apparatus described herein, the monitor arm is configured to rotate about the swivel axis over an arc of 270° or less.

In one or more embodiments of the extracorporeal blood treatment apparatus described herein, the monitor arm is configured to rotate about the swivel axis over an arc of 45° or more.

In one or more embodiments of the extracorporeal blood treatment apparatus described herein, a center of any arc of rotation of the monitor arm about the swivel axis is aligned with the front face of the housing such that when the monitor arm is in the middle of the arc of rotation, the monitor is in the front facing position.

In one or more embodiments of the extracorporeal blood treatment apparatus described herein, the base of the monitor mount rotates about the swivel axis and comprises a housing access aperture positioned such that the swivel axis passes through the housing access aperture; the monitor arm comprises a strut that comprises a base end attached to the base of the monitor mount, a monitor end attached to the monitor, and a base end aperture proximate the base end of the strut, wherein the strut is configured to rotate about the tilt axis, and wherein the base end aperture is positioned such that the tilt axis passes through the base end aperture; and wherein the first cable extends from the monitor through the housing access aperture of the base after passing through the base end aperture of the strut such that at least a portion of the first segment of the first cable is located between the base end aperture of the strut and the housing access aperture of the base. In one or more embodiments, the strut comprises an intermediate cable aperture located between the base end and the monitor end of the strut, wherein the first cable extends from the monitor through the intermediate cable aperture before reaching the base end aperture, and wherein the first cable enters the intermediate cable aperture from an interior side of the strut facing the swivel axis when moving along the first cable from the monitor towards the control unit. In one or more embodiments, the strut is offset from the swivel axis such that the swivel axis does not pass through the base end aperture of the strut.

In one or more embodiments of the extracorporeal blood treatment apparatus described herein, the base of the monitor mount rotates about the swivel axis and comprises a housing access aperture positioned such that the swivel axis passes through the housing access aperture; the monitor arm comprises a first strut and a second strut, wherein each of the first and second struts comprise a base end attached to the base of the monitor mount, a monitor end attached to the monitor, and a base end aperture proximate the base end of the strut, wherein each of the first and second struts is configured to rotate about the tilt axis, and wherein the base end aperture of each of the first and second struts is positioned such that the tilt axis passes through the base end aperture; wherein the first cable extends from the monitor through the housing access aperture of the base after passing through the base end aperture of the first strut such that at least a portion of the first segment of the first cable is located between the base end aperture of the strut and the housing access aperture of the base; wherein the apparatus comprises a second cable connecting the monitor to the control unit, wherein the first cable and the second cable comprise a cable bundle that bifurcates into the first cable and the second cable between the monitor and the control unit, wherein the second cable comprises a first segment generally aligned with the tilt axis and a second segment generally aligned with the swivel axis, wherein the first segment of the second cable is closer to the monitor that the second segment, wherein the second segment of the second cable is closer to the control unit than the first segment of the second cable, wherein the second segment of the second cable passes into the housing, and wherein the second cable extends from the monitor through the housing access aperture of the base after passing through the base end aperture of the second strut such that at least a portion of the first segment of the second cable is located between the base end aperture of the strut and the housing access aperture of the base; and further wherein the first segments of the first cable and the second cable are located on opposite sides of the swivel axis. In one or more embodiments, the second strut comprises an intermediate cable aperture located between the base end and the monitor end of the second strut, wherein the second cable extends from the monitor through the intermediate cable aperture of the second strut before reaching the base end aperture of the second strut, and wherein the second cable enters the intermediate cable aperture from an interior side of the second strut facing the swivel axis when moving along the second cable from the monitor towards the control unit.

In one or more embodiments of the extracorporeal blood treatment apparatus described herein, the monitor is configured to rotate about the tilt axis between the stowed position and the operating position when the monitor is in any one of the front-facing position, the left-facing position, and/or the right-facing position.

In one or more embodiments of the extracorporeal blood treatment apparatus described herein, a projection of the tilt axis along a direction aligned with the swivel axis intersects the housing access opening in the base.

In one or more embodiments of the extracorporeal blood treatment apparatus described herein, a projection of the swivel axis along a direction aligned with the tilt axis intersects base end aperture of the strut.

In one or more embodiments of the extracorporeal blood treatment apparatus described herein, the swivel axis intersects the tilt axis.

In one or more embodiments of the extracorporeal blood treatment apparatus described herein, a projection of the tilt axis on a plane containing the display surface when the monitor is in the operating position is located closer to a bottom edge of the monitor than a top edge of the monitor, wherein the bottom edge of the monitor is located closer to the top surface of the housing than the top edge of the monitor when the monitor is in the operating position.

In one or more embodiments of the extracorporeal blood treatment apparatus described herein, the monitor comprises a monitor height measured between a bottom edge and a top edge of the monitor, wherein the bottom edge of the monitor is located closer to the top surface of the housing than the top edge of the monitor when the monitor is in the operating position, and wherein a projection of the tilt axis on a plane containing the display surface when the monitor is in the operating position is located within a distance from the bottom edge of the monitor that is within 25% of the monitor height.

In one or more embodiments of the extracorporeal blood treatment apparatus described herein, the monitor mount comprises a shroud attached to the monitor arm, and wherein direct line of sight access to the housing access aperture and the first and second segments of the first cable is blocked by the shroud when the monitor is any allowable orientation relative to the housing.

In one or more embodiments of the extracorporeal blood treatment apparatus described herein, the monitor mount may include a shroud attached to the monitor arm, wherein direct line of sight access to the housing access aperture and the first and second cables is blocked by the shroud when the monitor is any allowable orientation relative to the housing.

In a second aspect, methods of manipulating the monitor on an extracorporeal blood treatment apparatus as described herein may include: moving the monitor and the monitor arm from the operating position to the stowed position; moving the extracorporeal blood treatment apparatus across a floor while the monitor and monitor arm are in the stowed position; and moving the monitor and the monitor arm from the stowed position to the operating position after moving extracorporeal blood treatment apparatus across the floor.

In one or more embodiments of the methods described herein, the method further includes rotating the monitor and the monitor arm about the swivel axis to move the monitor between the front-facing position and at least one of the left-facing position and the right-facing position.

In one or more embodiments of the methods described herein, the method further includes rotating the monitor and the monitor arm about the swivel axis to move the monitor between the front-facing position, the left-facing position, and the right-facing position.

As used herein and in the appended claims, the singular forms "a," "an," and "the" include plural referents unless the context clearly dictates otherwise. Thus, for example, reference to "a" or "the" component may include one or more of the components and equivalents thereof known to those skilled in the art. Further, the term "and/or" means one or all of the listed elements or a combination of any two or more of the listed elements.

It is noted that the term "comprises" and variations thereof do not have a limiting meaning where these terms appear in the accompanying description. Moreover, "a," "an," "the," "at least one," and "one or more" are used interchangeably herein.

The above summary is not intended to describe each embodiment or every implementation of the extracorporeal blood treatment apparatus as described herein.

Rather, a more complete understanding of the invention will become apparent and appreciated by reference to the following Description of Illustrative Embodiments and claims in view of the accompanying figures of the drawing.

DESCRIPTION OF ILLUSTRATIVE EMBODIMENTS

Figure 1:
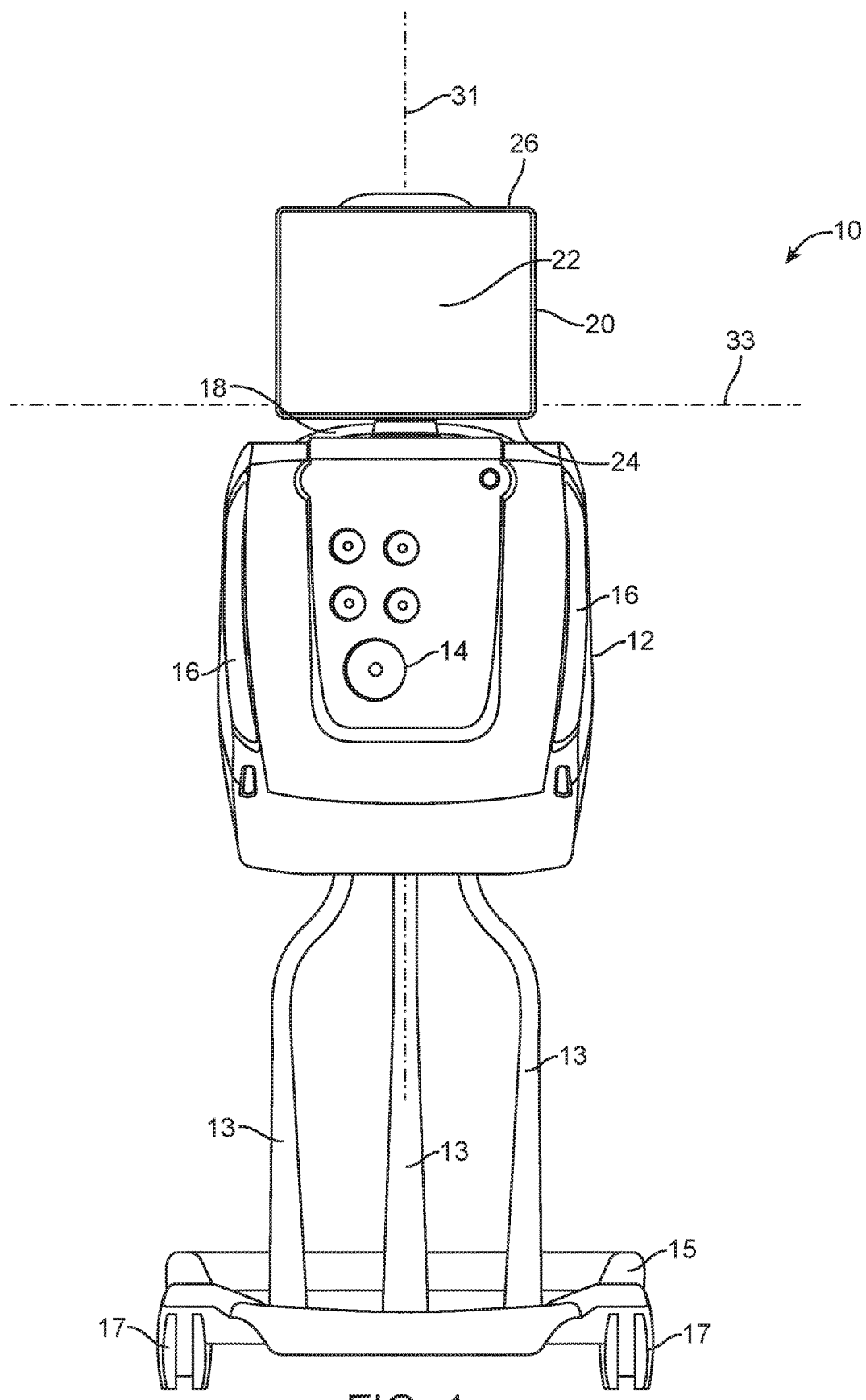
FIG. 1 is a view of the front of one embodiment of an extracorporeal blood treatment apparatus including a monitor and monitor mount as described herein.

In the following description of illustrative embodiments, reference is made to the accompanying figures of the drawing which form a part hereof, and in which are shown, by way of illustration, specific embodiments. It is to be understood that other embodiments may be utilized and structural changes may be made without departing from the scope of the present invention.

Figure 2:
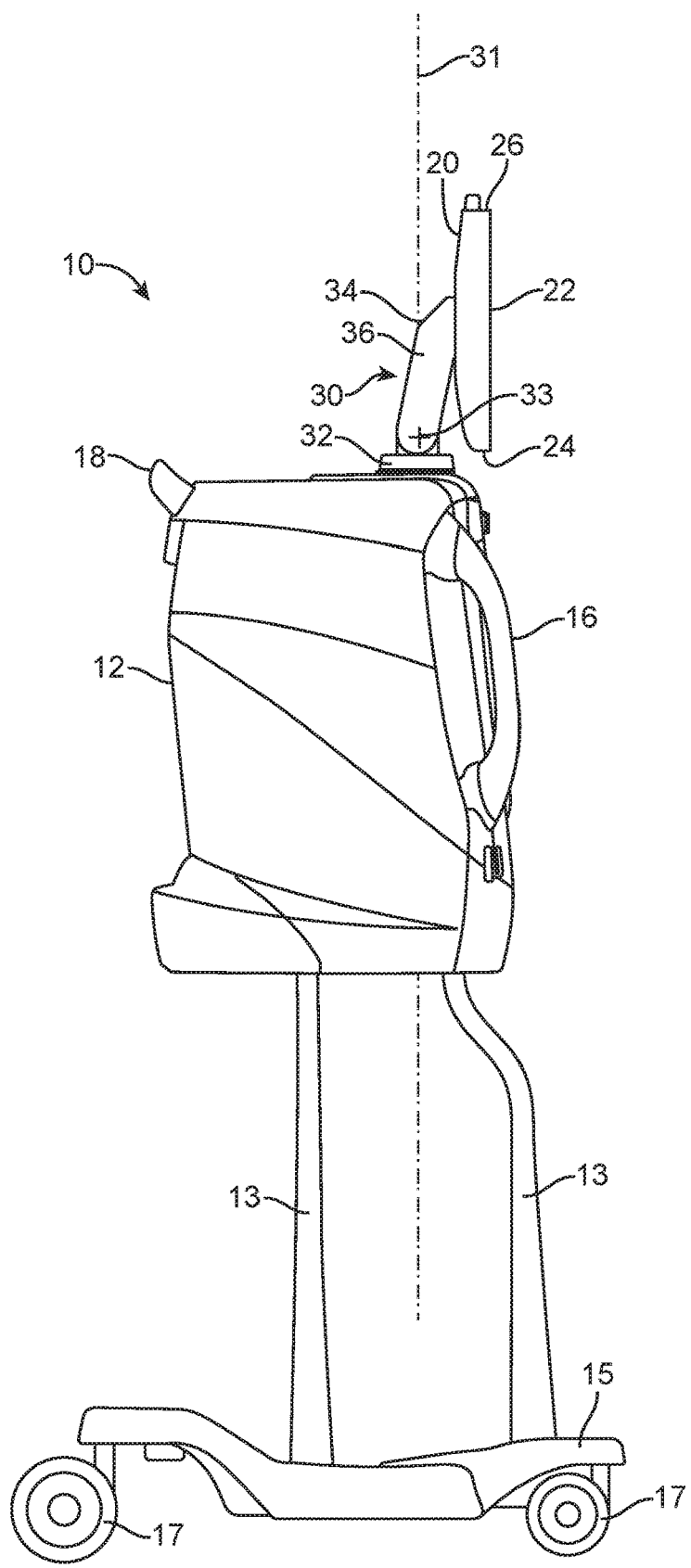
FIG. 2 is a left side view of the extracorporeal blood treatment apparatus depicted in FIG. 1.
Figure 3:
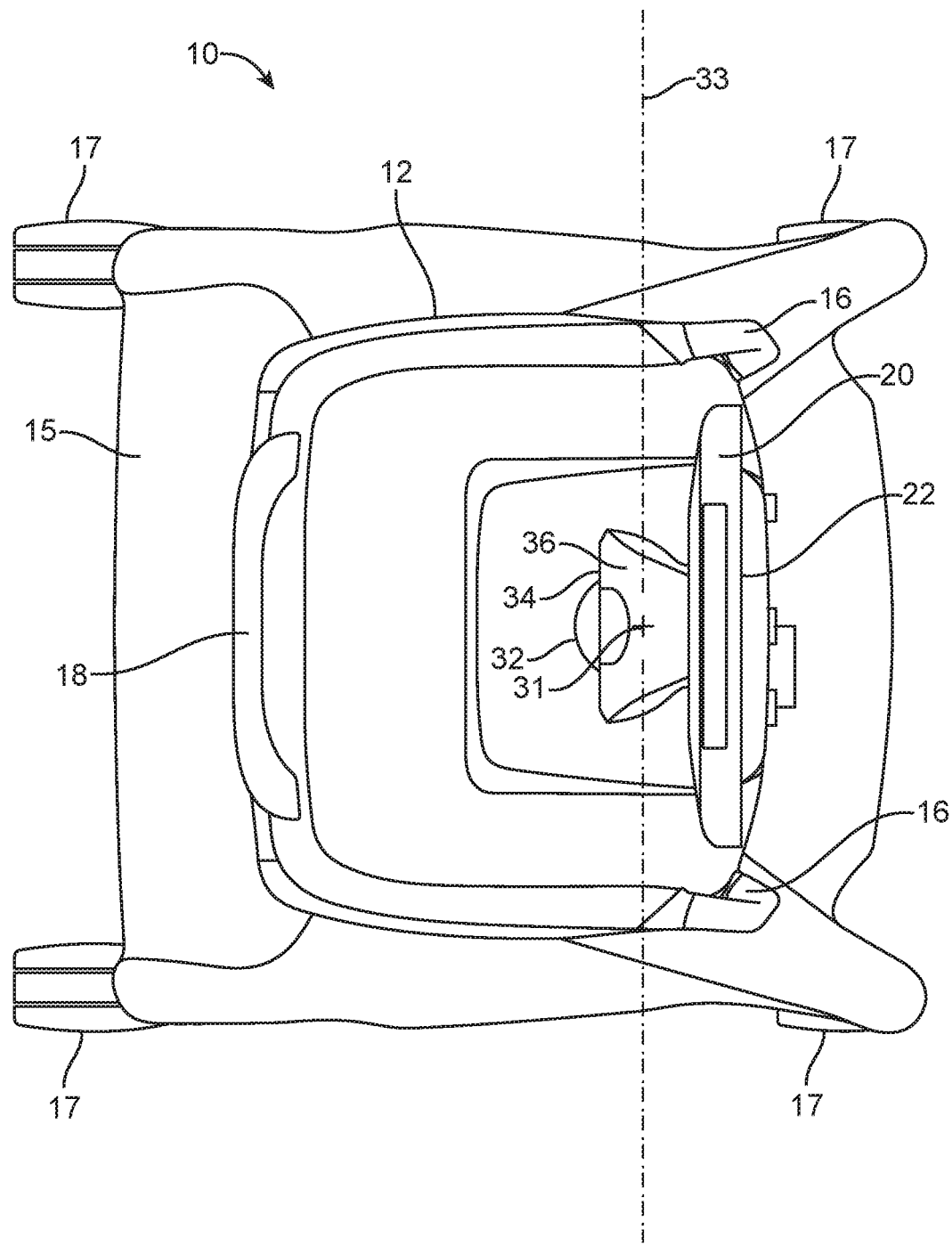
FIG. 3 is a top view of the extracorporeal blood treatment apparatus as depicted in FIGS. 1 and 2.

Referring to FIGS. 1-3, one illustrative embodiment of an extracorporeal blood treatment apparatus 10 is depicted. The apparatus 10 includes a housing 12 having one or more pumps 14 located on a front face of the housing 12. The one or more pumps 14 may, in one or more embodiments, be configured to move blood, treatment solution, effluent, etc. during extracorporeal blood treatment performed using the extracorporeal blood treatment apparatus 10. Although the pumps 14 are depicted in the form of peristaltic pumps, the pumps used in the extracorporeal blood treatment apparatus described herein may be provided in a variety of alternative forms, e.g., piston pumps, diaphragm pumps, etc. Other features depicted in connection with the illustrative embodiment of extracorporeal blood treatment apparatus 10 are front handles 16 and rear handle 18, along with legs 13 extending upward from base 15 to which wheels 17 are mounted.

The extracorporeal blood treatment apparatus described herein may, in one or more embodiments, also include a monitor 20 having a display surface 22 used to convey information in the form of visual images to a user. In one or more embodiments, the monitor 20 and display surface 22 may also be used as an input device to control operation of the extracorporeal blood treatment apparatus 10 when the monitor 20 is in the form of a touchscreen capable of accepting command inputs through physical contact with the display surface 22.

In one or more embodiments, the extracorporeal blood treatment apparatus includes a monitor mount 30 used to attach the monitor 20 to the extracorporeal blood treatment apparatus 10. The monitor mount 30 may include a base 32 attached to a top surface of the housing 12 and a monitor arm 34 extending from the base 32 to the monitor 20 (see, e.g., FIG. 2). The monitor 20 is positioned above the base 32 and the top surface of the housing 12 when attached to the extracorporeal blood treatment apparatus 10 by the depicted illustrative embodiment of monitor mount 30.

The monitor arm 34 is, in one or more embodiments, configured to rotate about a swivel axis 31 that is oriented vertically through the base 32 of the monitor mount 30 and the top surface of the housing 12. When so mounted, the monitor 20 can, in one or more embodiments, be rotated between a front facing position, a left facing position, and a right facing position.

In one or more embodiments, the monitor mount 30 may be configured to allow rotation of the monitor 20 about the swivel axis 31 over any selected arc. For example, in one or more embodiments, the monitor mount 30 may be configured to allow rotation of the monitor 20 about the swivel axis 31 over an arc of 360° or less, 270° or less, 180° or less, 150° or less, 120° or less, 90° or less, etc. In one or more embodiments, the monitor mount 30 may be configured to allow rotation of the monitor 20 about the swivel axis 31 over an arc of 45° or more, 60° or more, 75° or more, 90° or more, etc. In one or more embodiments, the center of any arc of rotation about swivel axis 31 may be aligned with the front face of the housing 12 such that when the monitor 20 is in the middle of its arc of rotation, the monitor 20 is in the front facing position in which the display surface 22 faces in the same direction as the front face of the housing 12 of an extracorporeal blood treatment device as described herein.

Figure 4:
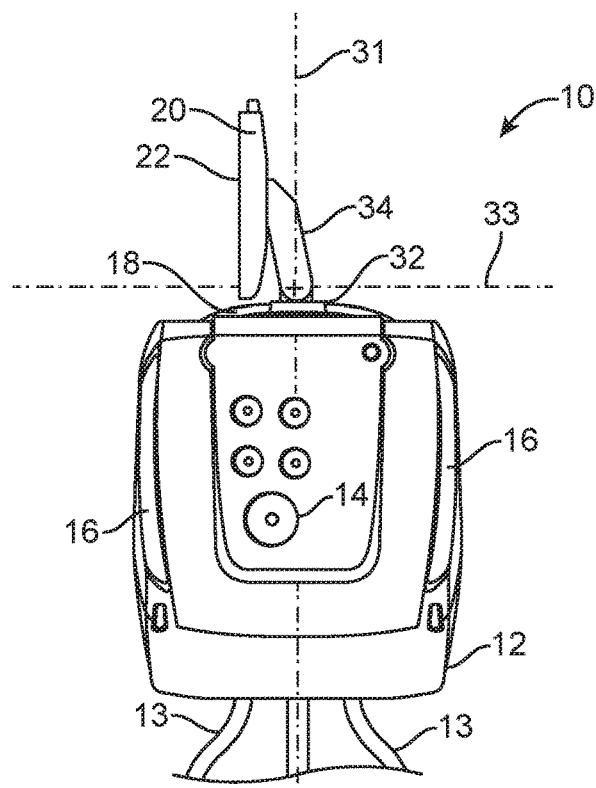
FIG. 4 is a frontal view of one illustrative embodiment of an extracorporeal blood treatment apparatus with the monitor rotated about a swivel axis to face the left side of the extracorporeal blood treatment apparatus.
Figure 5:
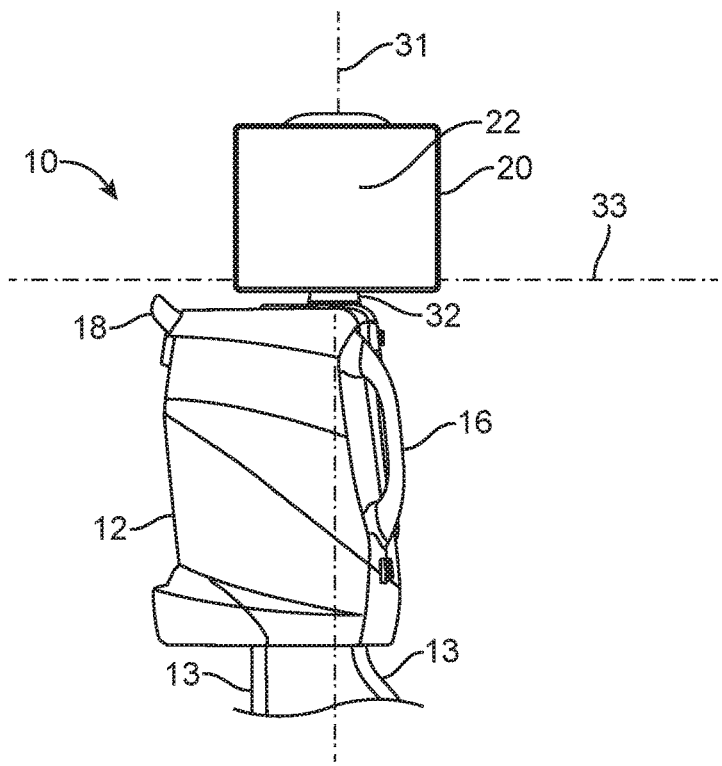
FIG. 5 is a left side view of the extracorporeal blood treatment apparatus depicted in FIG. 4.

In the left facing position, the monitor arm 34 is rotated about the swivel axis 31 such that the display surface 22 of the monitor 20 faces, in one or more embodiments, in the same direction as the left side of the housing 12 of the extracorporeal blood treatment apparatus 10. The monitor arm 34 and the monitor 20 are depicted in that orientation in FIGS. 4-5. In the left facing position, the display surface 22 of the monitor 20 may or may not be parallel with the left side of the housing 12. It may be sufficient that the display surface 22 of the monitor 20 be rotated toward the left side of the housing 12 to a point at which a user standing on the left side of the extracorporeal blood treatment apparatus can see and, if necessary, use the monitor 20 during operation of the apparatus.

In the right facing position, the monitor arm 34 is rotated about the swivel axis 31 such that the display surface 22 of the monitor 20 faces in the same direction as the right side of the housing 12 of the extracorporeal blood treatment apparatus 10. As with the left facing position, the display surface 22 of the monitor 20 may or may not be parallel with the right side of the housing 12. It may be sufficient that the display surface 22 of the monitor 20 be rotated toward the right side of the housing to a point at which a user standing on the right side of the extracorporeal blood treatment apparatus can see and, if necessary, use the monitor during operation of the apparatus.

The depicted embodiment of extracorporeal blood treatment apparatus 10 includes a monitor 20 and monitor mount 30 that are configured to allow rotation of the monitor about the swivel axis 31 such that the display surface 22 of the monitor 20 can move from the left facing position in which the display surface 22 faces in the same direction as the left side of the housing 12 and a right facing position in which the display surface 22 faces in the same direction as the right side of the housing 12. In one or more alternative embodiments, however, the monitor 20 and monitor mount 30 may be configured to allow greater or lesser rotation of the monitor 20 about the swivel axis 31. For example, in one or more embodiments, the monitor 20 may be configured to rotate to only one of the left facing position or the right facing position from the front facing position (where, for example, the extracorporeal blood treatment apparatus 10 is constructed such that rotation of the monitor to one side is not required for operation because an operator would not need to stand on that side of the housing to operate the apparatus).

In one or more alternative embodiments, the monitor 20 may be configured to rotate to a rear facing position in which the display surface 22 of the monitor 20 faces in the same direction as a rear of the housing 12. In one or more embodiments in which the monitor 20 may be configured to rotate to a rear facing position, the monitor 20 may reach that rear facing position by passing through either or both of the left facing position and the right facing position depending on the specific configuration and needs of the extracorporeal blood treatment apparatus 10 on which the monitor 20 is mounted.

In addition to allowing rotation about a vertically oriented swivel axis 31, the monitor mount 30 of the extracorporeal blood treatment apparatus 10 described herein may, in one or more embodiments, also allow for rotation of the monitor 20 about a tilt axis 33 that is oriented transverse to the swivel axis 31. Rotation of the monitor 20 about a tilt axis 33 may allow an operator to adjust the orientation of the display surface 22 so that it is more easily viewed by operators of different heights. Although the tilt axis 33 is described as being oriented transverse to the swivel axis 31, the relationship between the axes may or may not be perpendicular, i.e., the orientation of the axes relative to each other may vary, but will generally be transverse (e.g., the axes may form an angle of 80° to 100° when the axes are projected onto a vertical plane containing the swivel axis 31).

In one or more embodiments, the extracorporeal blood treatment apparatus 10 may be moved within a healthcare facility by an operator using one or both of the front handles 16 and/or the rear handle 18 to manipulate the apparatus 10 into position near a patient, through doorways, in hallways, into and out of elevators, etc. Moving the extracorporeal blood treatment apparatus 10 may, however, pose challenges if the height of the apparatus 10 with the monitor 20 in an upright position (as seen in, e.g., FIG. 1) interferes with the vision of a person moving the apparatus 10.

Figure 6:
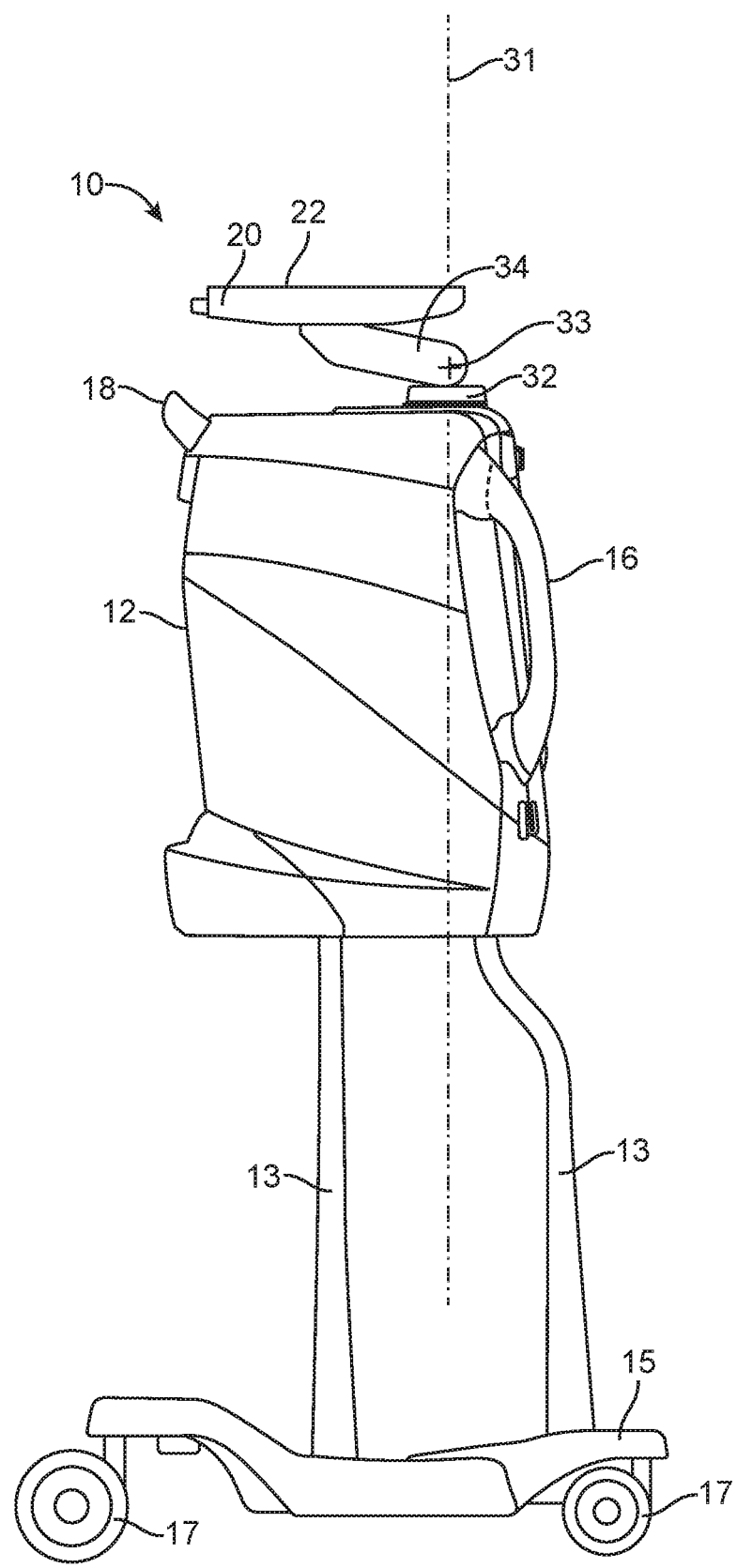
FIG. 6 is a left side view of the illustrative embodiment of an extracorporeal blood treatment apparatus with the monitor rotated to one embodiment of a stowed position from an operating position (as depicted in of FIGS. 1-3) after rotation of the monitor and monitor arm about a tilt axis as described herein.

To address that issue, the extracorporeal blood treatment apparatus described herein may include a monitor mount 30 that may, in one or more embodiments, be configured to allow rotation of the monitor 20 and monitor arm 34 about a tilt axis 33 such that the display surface 22 can be rotated from a generally vertical orientation (as seen in, e.g., FIGS. 1-5) to a stowed position in which the display surface 22 of the monitor 20 is oriented generally horizontally as seen in, e.g., FIG. 6. In the stowed position, the monitor 20 typically provides a much lower profile and, therefore, may offer a significantly improved view to an operator moving the extracorporeal blood treatment apparatus 10 through a healthcare facility using the front handles 16 and/or the rear handle 18.

As used herein the term "generally horizontally" means that the display surface 22 is located in a plane that is generally transverse to the swivel axis 31 where the term "transverse" has the same meaning as used in connection with the orientation of the swivel and tilt axes relative to each other as described herein (i.e., the plane in which the display surface 22 is located may be perpendicular to the swivel axis 31 or it may be merely nearly perpendicular to that axis, e.g., the swivel axis 31 may form an angle of 80° to 100° with the plane in which the display surface 22 is located).

In the illustrative embodiment of extracorporeal blood treatment apparatus 10 as depicted in FIG. 6, the display surface 22 of the monitor 20 faces away from the top surface of the housing 12 of the extracorporeal blood treatment apparatus 10 when the monitor 20 and monitor arm 34 are manipulated into the stowed position. In one or more alternative embodiments, however, the monitor 20 and monitor arm 34 may be manipulated such that the display surface 22 of the monitor 20 faces downwardly towards the floor on which the apparatus 10 is located when in the stowed position. In still other embodiments, the monitor 20 and monitor arm 34 may be configured to allow either of the stowed positions, i.e., a stowed position in which the monitor 20 is rotated about tilt axis 33 such that the display surface 22 faces upwardly (as seen in, e.g., FIG. 6) or downwardly towards the floor on which the apparatus 10 is located.

In one or more embodiments, the monitor mount 30 may be configured to allow rotation of the monitor 20 about the tilt axis 33 over any selected arc. For example, in one or more embodiments, the monitor mount may be configured to allow rotation of the monitor arm 34 and the monitor 20 about the tilt axis 33 over an arc of 180° or less, 150° or less, 120° or less, 90° or less, etc. In one or more embodiments, the monitor mount 30 may be configured to allow rotation of the monitor 20 about the tilt axis 33 over an arc of 45° or more, 60° or more, 75° or more, etc.

In one or more embodiments, the tilt axis 31 may be located proximate a bottom edge 24 of the monitor 20 where "proximate" means that the tilt axis 31 is located closer to the bottom edge 24 of the monitor 20 than the top edge 26 of the monitor 20 (with the bottom edge 24 of the monitor 20 being located closest to the top surface of the housing 12 of the extracorporeal blood treatment apparatus 10 when the monitor 20 and the display surface 22 are in generally vertical orientation as seen in, e.g., FIGS. 1-2). In one or more embodiments, the monitor 20 may have a monitor height as measured between the bottom edge 24 and the top edge 26 of the monitor 20, and the tilt axis 31 may be described as being located within a distance from the bottom edge 24 of the monitor 20 that is within 25% of the monitor height. Locating the tilt axis 31 closer to the bottom edge 24 rather than the top edge 26 of the monitor 20 may result in a lower profile for the monitor 20 and monitor arm 34 when in the stowed position as described herein.

As seen in, e.g., FIGS. 2-4 and 6, the extracorporeal blood treatment apparatus 10 described herein may include a monitor arm 34 that is covered by a shroud 36 such that direct line of sight access of the interior components of the monitor arm 34 and any cabling connecting the monitor 20 to components in the housing of the extracorporeal blood treatment apparatus 10 is not allowed. Covering the interior components of the monitor arm 34 with a shroud that prevents direct line of sight access of the interior components of the monitor arm (e.g., cabling, struts, etc.) during normal use and may, in one or more embodiments, prevent or at least significantly restrict entry of any cleaning solutions used to disinfect the extracorporeal blood treatment apparatus 10 into the interior of the housing 12.

As discussed herein, routing of cabling from a monitor to a control unit located within a housing of an extracorporeal blood treatment apparatus as described herein may be problematic if the cabling is routed such that it is subject to repeated flexing, tension, and/or compression during movement of the monitor about one or both of the swivel axis and tilt axis. For example, such movements, when repeated over time, may eventually damage the cabling, which could result in short or open circuits.

In one or more embodiments of the extracorporeal blood treatment apparatus described herein, stress on the cabling extending between a monitor and a control unit in a housing of the apparatus may be reduced by routing the cabling such that a segment of the cabling is generally aligned along the tilt axis before the cabling turns to enter the housing of the extracorporeal blood apparatus, where it is generally aligned along the swivel axis. Such routing of the cabling may reduce forces applied to the cabling during rotation of the monitor about the swivel and/or tilt axes.

Figure 7:
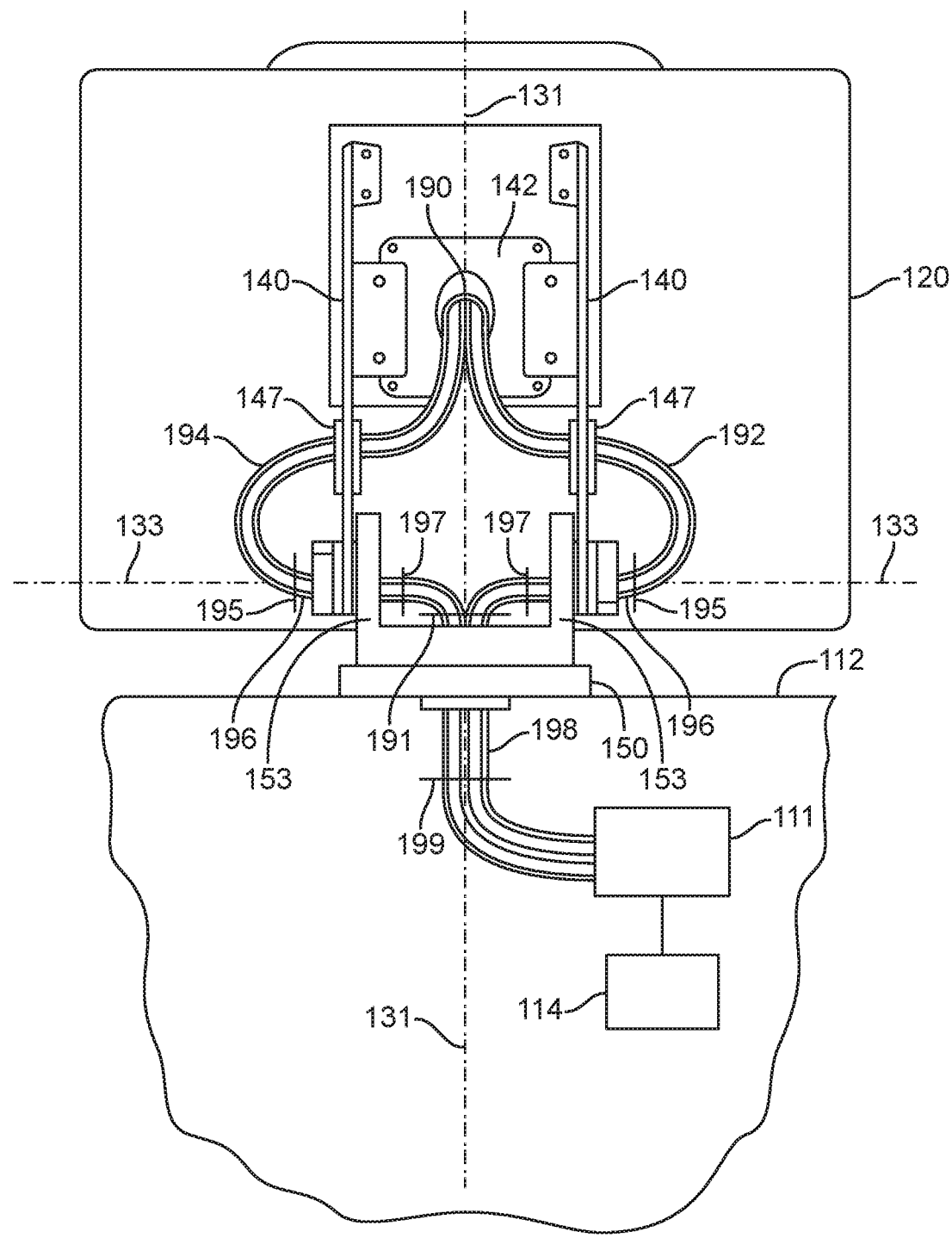
FIG. 7 is a view of the rear of one embodiment of a monitor and monitor mount with the shrouds removed to expose the interior components and cabling extending between the monitor and a control unit located in the interior of the housing of an extracorporeal blood treatment apparatus as described herein.

One illustrative embodiment of such an arrangement is depicted in FIG. 7 in which the interior components of a monitor arm as described herein are visible as mounted on the rear of a monitor 120. The components of the monitor arm include one or more struts 140 that extend upwardly from a base 150 located on a top surface of a housing 112. In the depicted embodiment, cable bundle 190 connects the monitor 120 to a control unit 111 located within the interior of the housing 112. Also depicted in FIG. 7 is a pump 114 which may also be operably connected to the control unit 111.

The swivel axis 131 and the tilt axis 133 around which the monitor 120 rotates are also depicted in FIG. 7 to illustrate routing of the cabling as described herein. Typically, multiple cables will be used to connect the monitor 120 to the control unit 111 which is why cable bundle 190 extends between the monitor 120 and the control unit 111. In particular, the depicted embodiment of cable bundle 190 bifurcates into separate cable bundles 192 and 194 that are portions of the cable bundle 190 attached to the monitor 120 (and that, in the depicted embodiment, meet each other to re-form cable bundle 190 before reaching the control unit 111). Although both bifurcated cable bundles 192 and 194 are depicted as containing multiple cables, in one or more embodiments of the monitor mounts described herein the cable bundle 190 may bifurcate into such that one or both of bifurcated cable bundles 192 and 194 include only a single cable. In one or more embodiments, the bifurcated cable bundles 192 and 194 may be routed along paths that are symmetrical about the vertically oriented swivel axis 131.

In one or more alternative embodiments, the monitor 120 may be connected by a single cable extending from the monitor 120 to the control unit 111. In such an alternative embodiment, the single cable would still include first and second segments aligned along the swivel and tilt axes as described herein.

The cable bundles 192 and 194 connecting the monitor 120 to the control unit 111 will, regardless of the number of cables contained therein, each include a first segment 196 that is generally aligned with the tilt axis 133 and a second segment 198 that is generally aligned with the swivel axis 131. In one or more embodiments, the second segment 198 may be described as being located closer to the control unit 111 than the first segment 196. In other words, when advancing along the cables from the monitor 120 to the control unit 111, the first segment 196 would be encountered first, followed by the second segment 198.

The cable bundles 192 and 194 may, in one or more embodiments such as, e.g., the depicted illustrative embodiment, enter apertures in the monitor arm assembly from opposite directions along the tilt axis 133. The first segments 196 of the cable bundles 192 and 194 may, in one or more embodiments, be described as being located on opposite sides of the swivel axis 131.

In the depicted illustrative embodiment, the first segments 196 of cable bundles 192 and 194 may be defined by endpoints 195 and 197. It will, however, be understood that the precise location of these endpoints may vary between different embodiments of the extracorporeal blood treatment apparatus described herein. Regardless of the specific location of the endpoints 195 and 197, however, the first segments 196 of the cable bundles 192 and 194 located between endpoints 195 and 197 will be generally aligned along the tilt axis 133. As used herein, the term "generally aligned" may mean that the first segment 196 of cabling 190 is co-linear with the tilt axis 133, but a perfectly co-linear relationship is not required.

Also in the depicted illustrative embodiment, the second segments 198 of cable bundles 192 and 194 may be generally defined by endpoints 191 and 199. As with the first segments 196, it will, however, be understood that the precise location of these endpoints may vary between different embodiments of the extracorporeal blood treatment apparatus described herein. Regardless of the specific location of the endpoints 191 and 199, however, the second segments 198 of the cable bundles 192 and 194 will be generally aligned with the swivel axis 131 where the term "generally aligned" has the same meaning as discussed above with respect to the first segment 196. The second segments 198 of each of the cable bundles 192 and 194 are located closer to the control unit 111 than the first segments 196 of the cable bundles 192 and 194. In one or more embodiments, it is the second segments 198 of the cable bundles 192 and 194 meet each other to re-form cable bundle 190 proximate the location where the cables pass into the housing 112 of the extracorporeal blood treatment apparatus.

Rotational operation of the interior components of the illustrative embodiment of the monitor mount as depicted in FIG. 7 includes rotation of the base of the monitor mount about swivel axis 131. In one or more embodiments, the base 150 includes a housing base bore 158 (see FIG. 8) positioned such that the cable bundle 190 (including cable bundles 192 and 194) and the swivel axis 131 pass through the housing base bore 158. Rotating the base 150 of the monitor mount about swivel axis 131 is accompanied by corresponding rotation of the monitor 120 and monitor arm components about the swivel axis 131.

Rotational operation of the interior components of the monitor mount as depicted in FIG. 7 also includes rotation of the struts 140 about the tilt axis 133. Rotating the struts 140 of the monitor mount about tilt axis 133 is accompanied by corresponding rotation of the monitor 120 about the tilt axis 133. In one or more embodiments of the monitor mounts as described herein, one or both of the struts 140 may be offset from the swivel axis 131 such that the swivel axis 131 does not pass through a base end aperture 167 of the strut 140 (see description of the base end aperture 167 of a strut 140 below).

In those embodiments in which the monitor mounted on the extracorporeal blood treatment apparatus is a touchscreen, control over the force required to rotate the monitor about the swivel and tilt axes may be helpful to limit unwanted movement of the monitor when an operator is entering commands on a GUI displayed on the touchscreen. In one or more embodiments, the monitor mount may be configured to provide selected levels of friction to control the force needed to rotate the monitor about the swivel and/or tilt axes.

Figure 8:
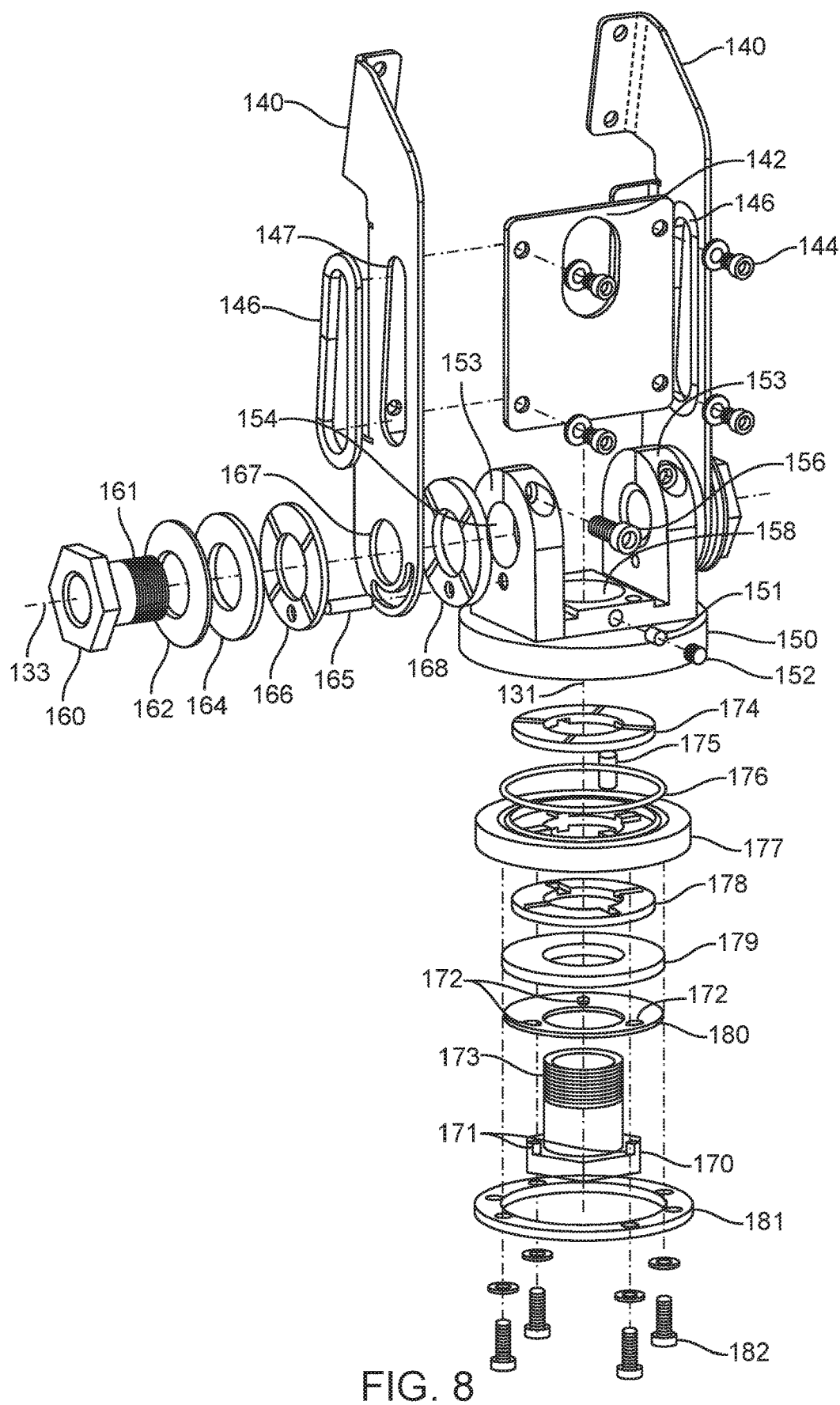
FIG. 8 is an exploded assembly diagram depicting one illustrative embodiment of a monitor mount as used in one or more embodiments of the extracorporeal blood treatment apparatus described herein.

One illustrative embodiment of the interior components of a monitor mount that includes two struts mounted to a base, with the base configured for rotation about a swivel axis and the struts configured for rotation about a tilt axis as described herein is depicted in the exploded assembly diagram of FIG. 8. The mechanism as depicted in FIG. 8 includes components depicted as an exploded assembly that are, when assembled, configured to allow the base 150 of the monitor mount to rotate about swivel axis 131 as described herein. The depicted mechanism also includes components depicted as an exploded assembly to the left of the arm 153 that, when assembled, are configured to allow the left strut 140 to rotate about the tilt axis 133.

Figure 9:
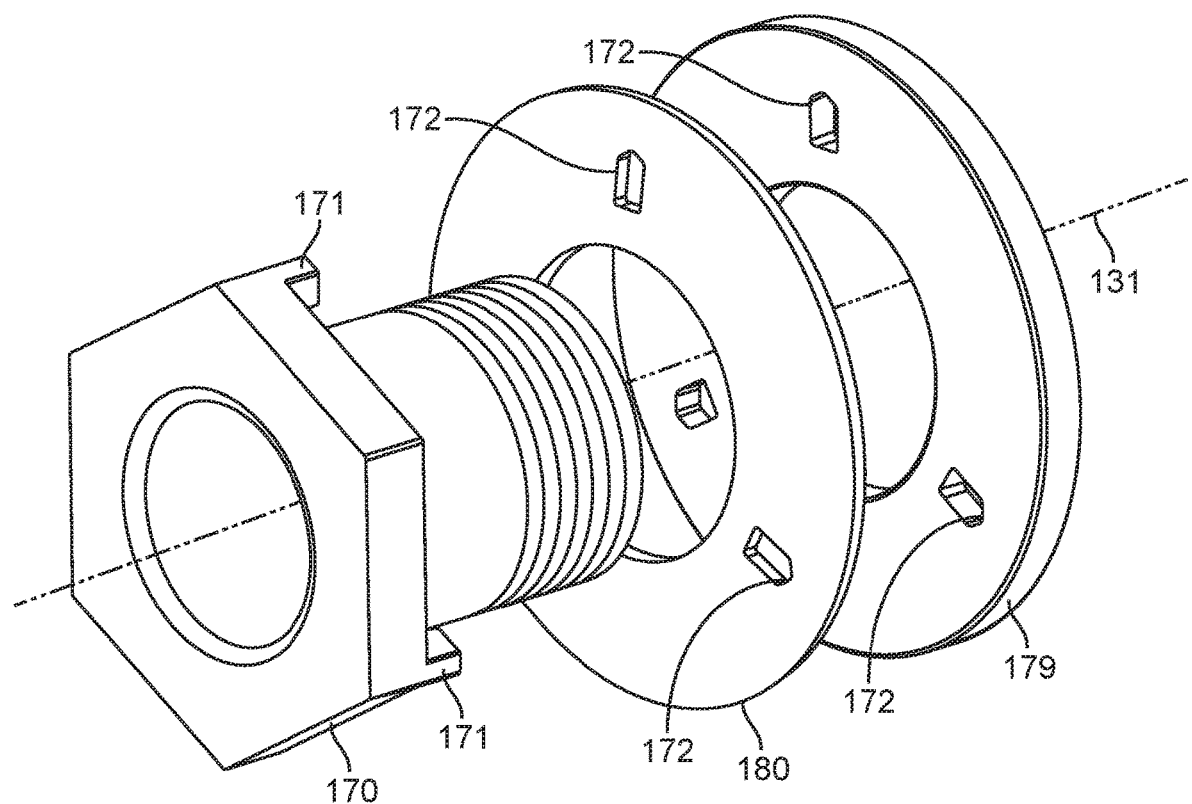
FIG. 9 is an enlarged view of a portion of the exploded assembly diagram of FIG. 8 depicting the base lock nut 170, concave spring washer 180 and wear disk 179.

The components located below the base 150 include a base lock nut 170, a concave spring washer 180 (with the concavity formed by the washer 180 facing the base 150), a wear disk 179, a lower thrust bearing 178, a nut plate 177, an O-ring 176, a nut plate dowel pin 175, and an upper thrust bearing 174. As seen in, e.g., FIGS. 8 and 9, the base lock nut 170 includes raised protrusions 171 on the base lock nut 170 that are configured to engage with mating features such as, e.g., cutouts 172 on the spring washer 180 and the wear disk 179 to cause the base lock nut 170, spring washer 180 and wear disk 179 to rotate in unison around swivel axis 131. Such an arrangement may, in one or more embodiments, limit wear on the surfaces in contact between these components.

Figure 10:
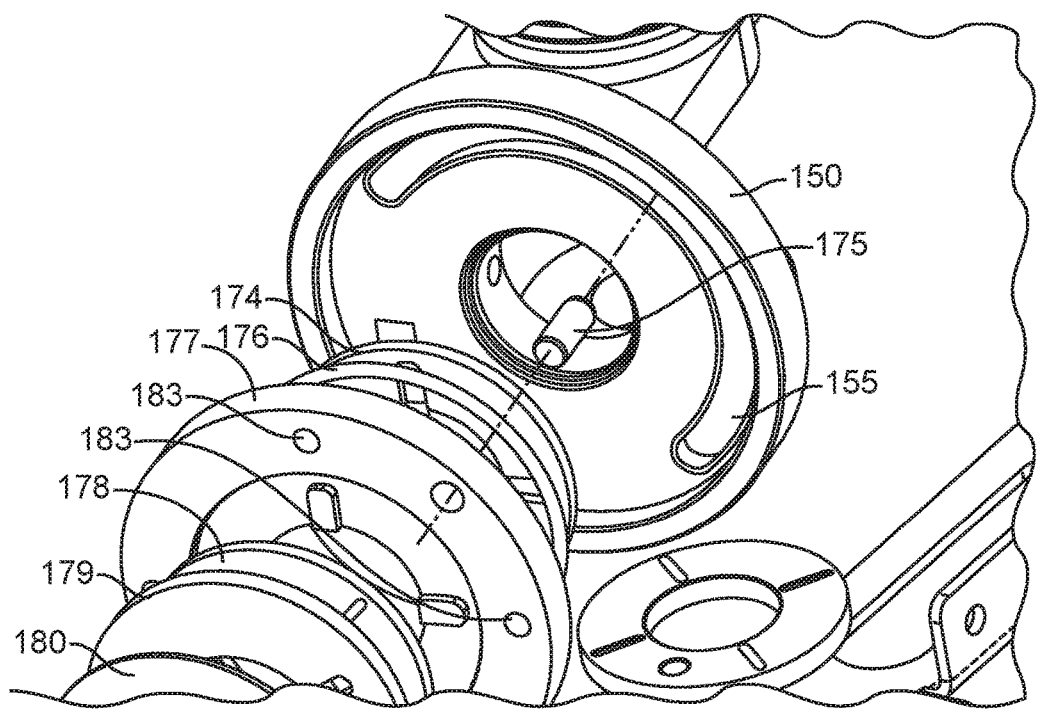
FIG. 10 is an enlarged view of a portion of the exploded assembly diagram of FIG. 8 depicting components below the base 150.

The components located below the base 150 also include, as seen in, e.g., FIGS. 8 and 10, the concave spring washer 180, wear disk 179, lower thrust bearing 178, a nut plate 177, an O-ring 176, a nut plate dowel pin 175, and an upper thrust bearing 174. The nut plate 177 is fixedly attached to the housing of the extracorporeal blood treatment apparatus using, in the depicted embodiment, fasteners 182 extending through fastening ring 181 and into threaded bores 183 (see, e.g., FIG. 10) in the nut plate 177. Furthermore, lower thrust bearing 178 and upper thrust bearing 174 are also fixed in position with the nut plate 177 due to the complementary mating features in the parts.

The dowel pin 175 is fitted into a bore in the nut plate 177 and extends into a slot 155 in the base 150 to restrict the arc over which the base 150 rotates about the swivel axis 131 (because the nut plate 177 is, as described herein, fixedly attached to the housing of the extracorporeal blood treatment apparatus). As discussed herein, that arc may vary in different embodiments of the monitor mounts as described herein.

When assembled, the components located between the base 150 and the base lock nut 170 are compressed and contained by the base lock nut 170 which is attached to the base 150 by threading threads 173 on the lock nut 170 with complementary threads (not shown) on the interior of the housing base bore 158. The rotational position of the lock nut 170 with respect to the housing base bore 158 is fixed using a pin 151 and a set screw 152 in the depicted embodiment. The pin 151 may, in one or more embodiments, be constructed of a material that is softer than the threads on the base lock nut 17, such that advancement of the set screw towards the pin 151 drives the pin 151 into the threads, with the pin 151 deforming, but not the threads on the lock nut 170. In one exemplary embodiment, the pin 151 may be formed of brass while the base lock nut 170 is formed of stainless steel.

When assembled, the components provide for rotation of the base 150 about the nut plate 177 which is attached in a stationary position to the housing of an extracorporeal blood treatment apparatus as described herein. In other words, the nut plate 177 of the depicted assembly does not rotate about the swivel axis 131 when the base 150 rotates about that axis.

In the depicted embodiment, the base lock nut 170 has a central bore which aligns with and forms a part of a housing access aperture that provides a path for the cabling to enter the interior of the housing of an extracorporeal blood treatment apparatus as described herein. As a result, cabling extending downward through the housing base bore 158 passes through the central bore of the lock nut 170 when passing through the housing access aperture of the monitor mount attached to a housing of an extracorporeal blood treatment apparatus as described herein.

The exploded assembly of components located to the left of the arm 153 to which the left strut 140 is attached allow for rotation of the left strut 140 about the tilt axis 133 when assembled. In one or more embodiments, the same set of assembled components may be used to attach the right strut 140 to the right base arm 153.

The components located to the left of the base arm 153 include a strut lock nut 160, a concave spring washer 162 (with the concavity formed by the washer 162 facing the base arm 153), a wear disk 164, and an outer thrust washer 166 located on an outside surface of the left strut 140 and aligned with the base end aperture 167 located in the strut 140. An inner thrust washer 168 is located between the base arm 153 and the inside surface of the strut 140. When the components along tilt axis 133 (as seen in, e.g., FIGS. 8 and 11) are assembled, a dowel pin 165 extends through a slot 186 formed in the strut 140 as well as openings 185 formed through the thrust washer 168 and the base arm 153. The dowel pin 165 also extends into a recess 185 in the wear disk 164. When assembled, the dowel pin 165 may be allowed to move along its length in translation through the openings 185 and slot 186 to allow for adjustment of the assembly. Rotation of the strut 140 about the tilt axis 133 is limited to an arc defined by the slot 186 formed around a portion of the base end aperture 167 in the strut 140. As discussed herein, that arc may vary in different embodiments of the monitor mounts as described herein.

When assembled together, the components aligned along the tilt axis 133 are compressed and contained by the strut lock nut 160 which is attached to the base arm 153 by threading threads 161 on the lock nut 160 with complementary threads (not shown) on the interior of the base arm bore 154. The rotational position of the lock nut 160 with respect to the bore 154 is fixed using a tilt locking screw 156 which compresses the lock nut 160 within the bore 154 when tightened. When assembled, the components provide for rotation of the strut 140 about the tilt axis 133 above the housing of an extracorporeal blood treatment apparatus as described herein.

Figure 11:
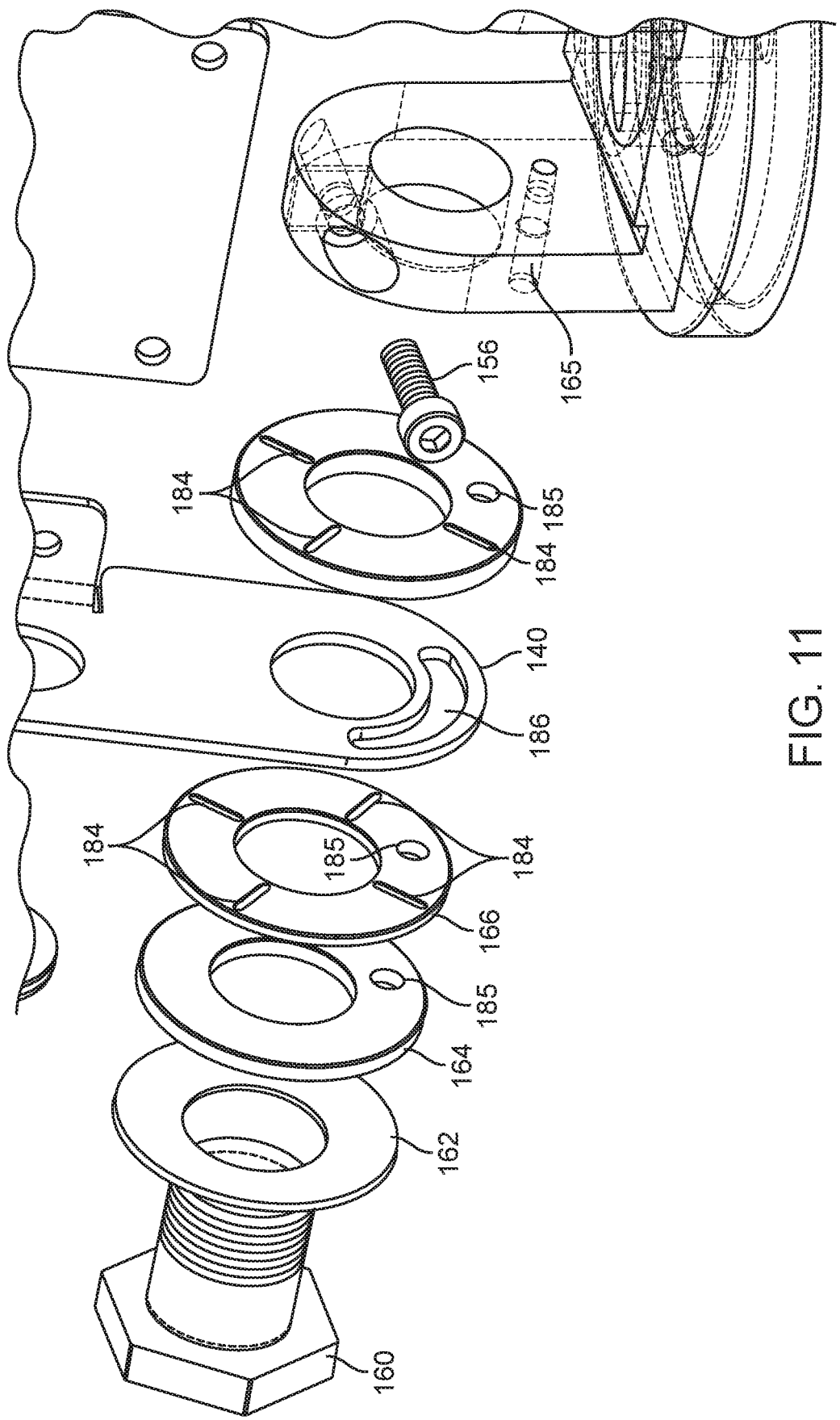
FIG. 11 is an enlarged view of a portion of the exploded assembly diagram of FIG. 8 depicting the components aligned along the tilt axis 133.

In one or more embodiments, the outer thrust washer 166 and the inner thrust washer 168 may include one or more lubricant reservoirs 184 to retain grease or a similar lubricant when the components aligned along the tilt axis 133 are assembled together. The lubricant reservoirs 184 may be in the form of radial slots in the washers 164 and 166 as seen in FIGS. 8 and 11, but other arrangements of lubricant reservoirs may also be provided. The lubricant retained in the lubricant reservoirs 184 may, in one or more embodiments, provide for reduced variation in the friction force during rotation of the monitor mount about the tilt axis 133 through the rated life of the monitor mounts as described herein.

In the depicted embodiment, the strut lock nut 160 has a central bore which aligns with base end aperture 167 provided in the strut 140 as described herein. As a result, cabling extending towards the swivel axis 131 from outside of the strut 140 (where outside is the side farthest away from the swivel axis 131) passes through the central bore of the strut lock nut 160 and through the base end aperture 167 formed in the strut 140.

The depicted embodiment of interior components of the monitor arm as depicted in FIG. 8 includes an optional monitor mount bridge 142 attached to both the left and right struts 140 by fasteners 144. The monitor mount bridge 142 may provide additional rigidity to the monitor arm when assembled with the struts 140.

In one or more embodiments of the monitor mounts as described herein, a cable bundle such as, e.g., cable bundle 194 in the depicted illustrative embodiment, extends from the monitor 120 through the housing base bore 158 of the base 150 after passing through the base end aperture 167 of the left strut 140 such that at least a portion of the first segment 196 of the cable bundle 194 is located between the base end aperture 167 of the left strut 140 and the housing access aperture 119 of the base 150. Cable bundle 192 follows, in the depicted illustrative embodiment, a similar path through the right strut 140.

In one or more embodiments of monitor mounts as described herein, such as, e.g., the depicted illustrative embodiment, each of the struts 140 may also include an intermediate cable aperture 147 along with a cable protector 146. Referring to, e.g., FIG. 7, one or both of the cable bundles 192 and 194 may, in one or more embodiments, be routed through an intermediate cable aperture 147 in one of the struts 140 before reaching and entering the bores formed in the strut lock nuts 160 (and the aligned base end apertures 167 in the struts 140). In one or more embodiments, one or both of the cable bundles 192 and 194 may enter the intermediate cable aperture 147 in a strut 140 from an interior side of the strut 140 (where the interior side of the strut 140 is the side of the strut 140 that faces the swivel axis 131) when moving along the cable bundle 192 or 194 from the monitor 120 towards the control unit 111.

As discussed herein, the force used to rotate monitors and monitor arms about the swivel axes and tilt axes as described herein may be controlled to limit unwanted movement of the monitor. In the illustrative embodiment of the components used to attach the base 150 to the nut plate 177 and the struts 140 to the base arms 153, rotation of the respective lock nuts can be used to adjust the forces required to rotate the components relative to each other.

Although one illustrative embodiment of structures used to control rotation of a monitor and monitor arm about a tilt axis and a swivel axis are depicted in FIGS. 7 and 8, many other structures could be used in place of those described herein and the present invention should not be limited to the specific arrangement of components in the depicted illustrative embodiment. One alternative structure may include one or more detent mechanisms to control rotation about one or both of the tilt and swivel axes.

The monitor mounts described herein include tilt and swivel axes that are arranged along with cables connecting a monitor to a control unit in a housing of an extracorporeal blood treatment apparatus such that the monitor can be rotated about the tilt and swivel axes. The tilt and swivel axes may have one or more selected arrangements with respect to each other and a housing access aperture, i.e., the aperture through which the cables enter the housing of the extracorporeal blood treatment apparatus.

Figure 12A:
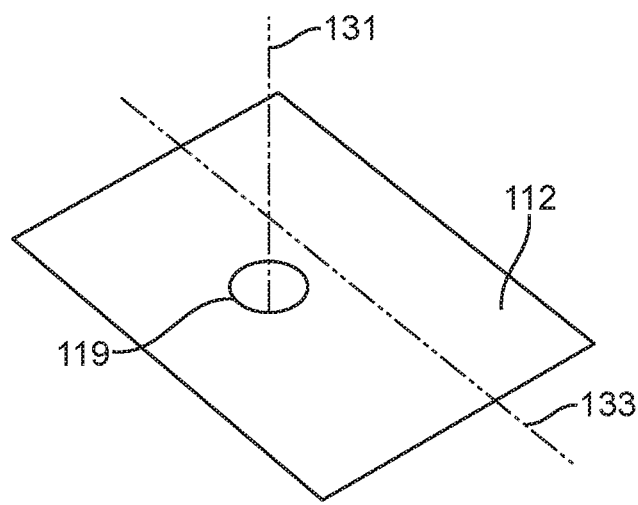
FIG. 12A is a schematic diagram depicting one illustrative arrangement of swivel and tilt axes relative to a housing access aperture in the housing of an extracorporeal blood treatment apparatus as described herein.
Figure 12B:
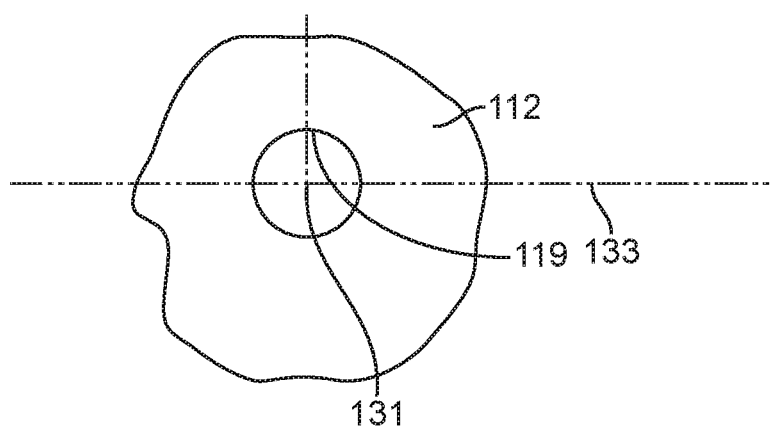
FIG. 12B is a view of the diagram of FIG. 12A taken along the direction of the swivel axis 131.

In one or more embodiments, a projection of the tilt axis along a direction aligned with the swivel axis intersects the housing access opening. A schematic diagram of one embodiment of such an arrangement is depicted in FIGS. 12A and 12B, where the swivel axis 131 is depicted as extending through the housing access aperture 119 in the housing 112 (which would be aligned with the housing base aperture 158 in the base 150 of the monitor mount as depicted in, e.g., FIG. 8). As best seen in FIG. 12B, a projection of the tilt axis 133 down onto the housing 112 would intersect the housing access aperture 119.

In one or more embodiments, a projection of the swivel axis along a direction aligned with the tilt axis intersects base end aperture of one or both of the struts of the monitor mount. One embodiment of such an arrangement can be seen in, e.g., FIG. 8, where a projection of the swivel axis 131 in either direction along the tilt axis 133 would extend through the base end aperture 167 of one of the struts 140.

In one or more embodiments of the monitor mounts described herein, the swivel axis may intersect the tilt axis. One illustrative example of this arrangement of swivel and tilt axes is depicted in, e.g., FIGS. 3, 4 and 6 (in which swivel axis 31 intersects tilt axis 33). Another illustrative example is depicted in FIG. 8 (in which swivel axis 131 intersects tilt axis 133).

As discussed herein, the monitor arms may include a shroud to prevent direct visual access to the components (e.g., cabling, support struts, etc.) of the monitor arm supporting a monitor on an extracorporeal blood treatment apparatus as described herein. In one or more embodiments, the shrouds may prevent direct line of sight access to the housing access aperture (located underneath/within the base of the monitor arm as discussed herein) and/or any cables (e.g., the first and second cables) connecting the monitor to components in the housing of an extracorporeal blood treatment apparatus as described herein. In one or more embodiments, the shrouds may also prevent or at least significantly restrict entry of liquids into the interiors of housings of extracorporeal blood treatment apparatus described herein (e.g., liquid cleaning solutions used to disinfect the extracorporeal blood treatment apparatus, etc.).

Figure 13:
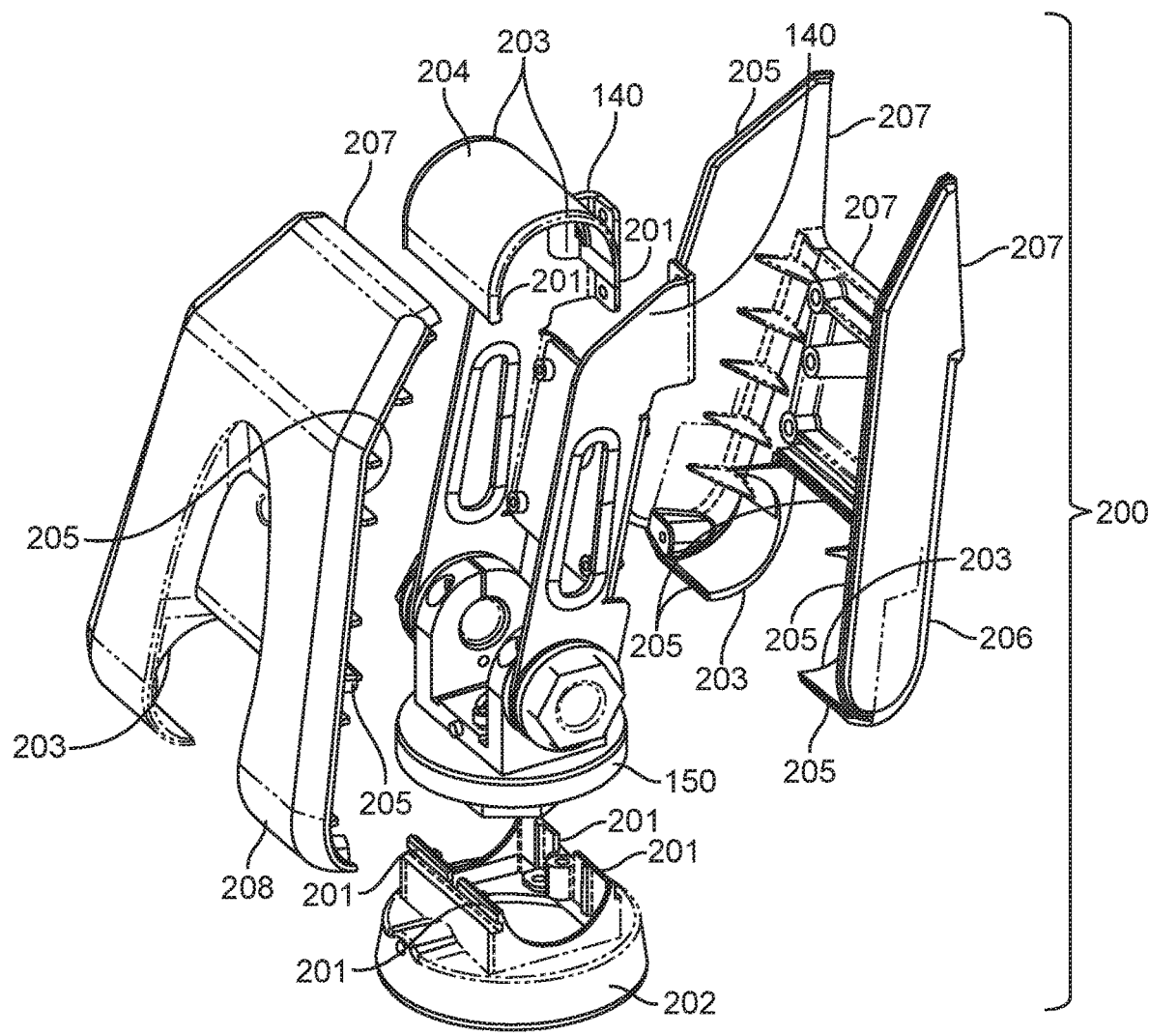
FIG. 13 is an exploded perspective view of one illustrative embodiment of a shroud assembly that can be used to shroud a monitor mount as described herein.

One illustrative embodiment of a shroud assembly that may be used to form a shroud in one or more embodiments of a monitor mount as described herein is depicted in FIG. 13. The depicted shroud assembly 200 is configured to cover a monitor arm that includes two struts 140 attached to base 150, with the shroud assembly 200 including a shroud base 202 and shroud base cable cover 204 configured to fit over the base 150 of the monitor arm in a manner that allows for the passage of cables as described herein. The shroud assembly 200 further includes a front shroud panel 206 and rear shroud panel 208 to enclose the struts 140 and the remainder of the base 150 not covered by the shroud base 202 and shroud base cable cover 204, as well as the struts 140 connecting a monitor (not shown) to the base 150.

The shroud base 202, shroud base cable cover 204, shroud front panel 206, and shroud rear panel 208 may, in one or more embodiments, be configured to (as discussed herein) to prevent direct line of sight access to the housing access aperture (located underneath/within the base 150 as discussed herein), the struts 140, and any cables (e.g., the first and second cables) connecting the monitor to components in the housing of an extracorporeal blood treatment apparatus as described herein. In one or more embodiments, the shrouds used on monitor mounts as described herein (such as, e.g., shroud assembly 200) may also prevent or at least significantly limit the entry of liquids into the interior of the housing of an extracorporeal blood treatment apparatus on which the monitor arm is located.

To accomplish those functions, i.e., prevent direct line of sight access and prevent or limit liquid from entering the housing, the shroud base cable cover 204 of the depicted illustrative embodiment of shroud assembly 200 is positioned between the struts 140 near the base 150 over a central portion of the shroud base 202. The shroud base 200 and shroud base cable cover 204 include complementary mating surfaces 201 configured to mate with each other to prevent direct line of sight access to the cables passing through that portion of the shroud assembly 200 regardless of the orientation of the monitor mount. The shroud base cable cover 204, front shroud panel 206, and rear shroud panel 208 also include complementary mating surfaces 203 configured to mate with each other and prevent direct line of sight access to the cables and the base 150 at each end of the shroud base cable cover 204 when assembled regardless of the orientation of the monitor mount. Further, front shroud panel 206 and rear shroud panel 208 include complementary mating surfaces 205 that mate with each to prevent direct line of sight access to the struts 140 between the base 150 and the monitor (not shown) that is supported by the struts 140. In the depicted illustrative embodiment, the front shroud panel 206 and rear shroud panel 208 include mating surfaces 207 configured to mate with corresponding mating surfaces on a monitor (not shown) attached to the struts 140.

The complete disclosure of the patents, patent documents, and publications identified herein are incorporated by reference in their entirety as if each were individually incorporated. To the extent there is a conflict or discrepancy between this document and the disclosure in any such incorporated document, this document will control.

Illustrative embodiments of extracorporeal blood treatment apparatus including monitors and monitor mounts configured to rotate about swivel and tilt axes are discussed herein with some possible variations described. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof. It should also be understood that this invention also may be suitably practiced in the absence of any element not specifically disclosed as necessary herein.

What is claimed is:

1. An extracorporeal blood treatment apparatus comprising:
   one or more pumps located on a front face of a housing, wherein the one or more pumps are configured to move blood and a treatment solution during extracorporeal blood treatment;
   a monitor comprising a display surface configured to display visual images thereon;
   a monitor mount comprising a base attached to a top surface of the housing and a monitor arm attached to base and the monitor, wherein the monitor is positioned above the base and the top surface of the housing, and wherein the monitor arm is configured to:
      rotate about a swivel axis that is oriented vertically through the base and the top surface of the housing such that the monitor can be rotated between a front-facing position in which the display surface faces the same direction as the front face of the housing and one of a left-facing position in which the display surface faces the same direction as a left side of the housing and a right-facing position in which the display surface faces the same direction as a right side of the housing;
      rotate about a tilt axis oriented transverse to the swivel axis, wherein the tilt axis is located above the base and the top surface of the housing, wherein the monitor is configured to rotate about the tilt axis between a stowed position and an operating position, wherein in the stowed position the display surface of the monitor is oriented in a plane that is generally transverse to the swivel axis, wherein in the operating position the display surface of the monitor is oriented in a plane that is generally aligned with the swivel axis;
   a control unit located within the housing and operably connected to the one or more pumps, wherein the control unit is configured to operate the one or more pumps to move blood and a treatment solution and the monitor; and
   a first cable connecting the monitor to the control unit, wherein the first cable comprises a first segment generally aligned with the tilt axis and a second segment generally aligned with the swivel axis, wherein the first segment is closer to the monitor that the second segment, and wherein the second segment is closer to the control unit than the first segment, and further wherein the second segment of the first cable passes into the housing.

2. An apparatus according to claim 1, wherein the apparatus comprises a second cable connecting the monitor to the control unit, wherein the first cable and the second cable comprise a cable bundle that bifurcates into the first cable and the second cable between the monitor and the control unit,
   and wherein the second cable comprises a first segment generally aligned with the tilt axis and a second segment generally aligned with the swivel axis, wherein the first segment of the second cable is closer to the monitor that the second segment, and wherein the second segment of the second cable is closer to the control unit than the first segment of the second cable, and further wherein the second segment of the second cable passes into the housing,
   and further wherein the first segments of the first cable and the second cable are located on opposite sides of the swivel axis.

3. An apparatus according to claim 2, wherein the first cable and the second cable combine to reform the cable bundle in the housing.

4. An apparatus according to claim 2, wherein the first segment of the first cable is symmetrical about the swivel axis with the first segment of the second cable, and wherein the second segment of the first cable is symmetrical about the swivel axis with the second segment of the second cable.

5. An apparatus according to claim 1, wherein the monitor arm is configured to rotate about the swivel axis between both the left-facing position and the right-facing position.

6. An apparatus according to claim 1, wherein the monitor arm is configured to rotate about the swivel axis over an arc of 270° or less.

7. An apparatus according to claim 1, wherein the monitor arm is configured to rotate about the swivel axis over an arc of 45° or more.

8. An apparatus according to claim 1, wherein a center of any arc of rotation of the monitor arm about the swivel axis is aligned with the front face of the housing such that when the monitor arm is in the middle of the arc of rotation, the monitor is in the front facing position.

9. An apparatus according to claim 1, wherein:
the base of the monitor mount rotates about the swivel axis and comprises a housing access aperture positioned such that the swivel axis passes through the housing access aperture;
the monitor arm comprises a strut that comprises a base end attached to the base of the monitor mount, a monitor end attached to the monitor, and a base end aperture proximate the base end of the strut, wherein the strut is configured to rotate about the tilt axis, and wherein the base end aperture is positioned such that the tilt axis passes through the base end aperture; and
wherein the first cable extends from the monitor through the housing access aperture of the base after passing through the base end aperture of the strut such that at least a portion of the first segment of the first cable is located between the base end aperture of the strut and the housing access aperture of the base.

10. An apparatus according to claim 9, wherein the strut comprises an intermediate cable aperture located between the base end and the monitor end of the strut, wherein the first cable extends from the monitor through the intermediate cable aperture before reaching the base end aperture, and wherein the first cable enters the intermediate cable aperture from an interior side of the strut facing the swivel axis when moving along the first cable from the monitor towards the control unit.

11. An apparatus according to claim 9, wherein the strut is offset from the swivel axis such that the swivel axis does not pass through the base end aperture of the strut.

12. An apparatus according to claim 1, wherein:
the base of the monitor mount rotates about the swivel axis and comprises a housing access aperture positioned such that the swivel axis passes through the housing access aperture;
the monitor arm comprises a first strut and a second strut, wherein each of the first and second struts comprise a base end attached to the base of the monitor mount, a monitor end attached to the monitor, and a base end aperture proximate the base end of the strut, wherein each of the first and second struts is configured to rotate about the tilt axis, and wherein the base end aperture of each of the first and second struts is positioned such that the tilt axis passes through the base end aperture;
wherein the first cable extends from the monitor through the housing access aperture of the base after passing through the base end aperture of the first strut such that at least a portion of the first segment of the first cable is located between the base end aperture of the strut and the housing access aperture of the base;
wherein the apparatus comprises a second cable connecting the monitor to the control unit, wherein the first cable and the second cable comprise a cable bundle that bifurcates into the first cable and the second cable between the monitor and the control unit,
wherein the second cable comprises a first segment generally aligned with the tilt axis and a second segment generally aligned with the swivel axis, wherein the first segment of the second cable is closer to the monitor that the second segment, wherein the second segment of the second cable is closer to the control unit than the first segment of the second cable, wherein the second segment of the second cable passes into the housing, and wherein the second cable extends from the monitor through the housing access aperture of the base after passing through the base end aperture of the second strut such that at least a portion of the first segment of the second cable is located between the base end aperture of the strut and the housing access aperture of the base;
and further wherein the first segments of the first cable and the second cable are located on opposite sides of the swivel axis.

13. An apparatus according to claim 12, wherein the second strut comprises an intermediate cable aperture located between the base end and the monitor end of the second strut, wherein the second cable extends from the monitor through the intermediate cable aperture of the second strut before reaching the base end aperture of the second strut, and wherein the second cable enters the intermediate cable aperture from an interior side of the second strut facing the swivel axis when moving along the second cable from the monitor towards the control unit.

14. An apparatus according to claim 1, wherein the monitor is configured to rotate about the tilt axis between the stowed position and the operating position when the monitor is in any one of the front-facing position, the left-facing position, and/or the right-facing position.

15. An apparatus according to claim 1, wherein a projection of the tilt axis along a direction aligned with the swivel axis intersects the housing access opening in the base.

16. An apparatus according to claim 1, wherein a projection of the swivel axis along a direction aligned with the tilt axis intersects base end aperture of the strut.

17. An apparatus according to claim 1, wherein the swivel axis intersects the tilt axis.

18. An apparatus according to claim 1, wherein a projection of the tilt axis on a plane containing the display surface when the monitor is in the operating position is located closer to a bottom edge of the monitor than a top edge of the monitor, wherein the bottom edge of the monitor is located closer to the top surface of the housing than the top edge of the monitor when the monitor is in the operating position.

19. An apparatus according to claim 1, wherein the monitor comprises a monitor height measured between a bottom edge and a top edge of the monitor, wherein the bottom edge of the monitor is located closer to the top surface of the housing than the top edge of the monitor when the monitor is in the operating position, and wherein a projection of the tilt axis on a plane containing the display surface when the monitor is in the operating position is located within a distance from the bottom edge of the monitor that is within 25% of the monitor height.

20. An apparatus according to claim 1, wherein the monitor mount comprises a shroud attached to the monitor arm, and wherein direct line of sight access to the housing access aperture and the first and second segments of the first cable is blocked by the shroud when the monitor is any allowable orientation relative to the housing.

21. An apparatus according to claim 2, wherein the monitor mount comprises a shroud attached to the monitor arm, and wherein direct line of sight access to the housing access aperture and the first and second cables is blocked by the shroud when the monitor is any allowable orientation relative to the housing.

22. An extracorporeal blood treatment apparatus comprising:
- one or more pumps located on a front face of a housing, wherein the one or more pumps are configured to move blood and a treatment solution during extracorporeal blood treatment;
- a monitor comprising a display surface configured to display visual images thereon;
- a monitor mount comprising a base attached to a top surface of the housing and a monitor arm attached to base and the monitor, wherein the monitor is positioned above the base and the top surface of the housing, wherein the base of the monitor mount rotates about the swivel axis and comprises a housing access aperture positioned such that the swivel axis passes through the housing access aperture, and wherein the monitor arm is configured to:
  - rotate about a swivel axis that is oriented vertically through the base and the top surface of the housing such that the monitor can be rotated between a front-facing position in which the display surface faces the same direction as the front face of the housing and one of a left-facing position in which the display surface faces the same direction as a left side of the housing and a right-facing position in which the display surface faces the same direction as a right side of the housing;
  - rotate about a tilt axis oriented transverse to the swivel axis, wherein the tilt axis is located above the base and the top surface of the housing, wherein the monitor is configured to rotate about the tilt axis between a stowed position and an operating position, wherein in the stowed position the display surface of the monitor is oriented in a plane that is generally transverse to the swivel axis, wherein in the operating position the display surface of the monitor is oriented in a plane that is generally aligned with the swivel axis;
- a control unit located within the housing and operably connected to the one or more pumps, wherein the control unit is configured to operate the one or more pumps to move blood and a treatment solution and the monitor;
- a first cable connecting the monitor to the control unit, wherein the first cable comprises a first segment generally aligned with the tilt axis and a second segment generally aligned with the swivel axis, wherein the first segment is closer to the monitor that the second segment, and wherein the second segment is closer to the control unit than the first segment, and further wherein the second segment of the first cable passes into the housing; and
- a second cable connecting the monitor to the control unit, wherein the first cable and the second cable comprise a cable bundle that bifurcates into the first cable and the second cable between the monitor and the control unit, wherein the second cable comprises a first segment generally aligned with the tilt axis and a second segment generally aligned with the swivel axis, wherein the first segment of the second cable is closer to the monitor that the second segment, and wherein the second segment of the second cable is closer to the control unit than the first segment of the second cable, and further wherein the second segment of the second cable passes into the housing;
- wherein the first segments of the first cable and the second cable are located on opposite sides of the swivel axis;
- wherein the monitor arm comprises a strut that comprises a base end attached to the base of the monitor mount, a monitor end attached to the monitor, and a base end aperture proximate the base end of the strut, wherein the strut is configured to rotate about the tilt axis, and wherein the base end aperture is positioned such that the tilt axis passes through the base end aperture;
- wherein the first cable extends from the monitor through the housing access aperture of the base after passing through the base end aperture of the strut such that at least a portion of the first segment of the first cable is located between the base end aperture of the strut and the housing access aperture of the base;
- wherein a projection of the tilt axis along a direction aligned with the swivel axis intersects the housing access opening in the base;
- and wherein a projection of the swivel axis along a direction aligned with the tilt axis intersects base end aperture of the strut.

* * * * *